(12) United States Patent
Zaidi et al.

(10) Patent No.: US 11,246,861 B1
(45) Date of Patent: *Feb. 15, 2022

(54) GSNO REDUCTASE INHIBITOR AS AN ADJUNCT THERAPY WITH REMOTE ISCHEMIC CONDITIONING AND THROMBOLYTIC REPERFUSION THERAPIES IN STROKE

(71) Applicant: KING ABDULAZIZ UNIVERSITY, Jeddah (SA)

(72) Inventors: Syed Kashif Zaidi, Jeddah (SA); Md. Nasrul Hoda, Phoenix, AZ (US); Muhammad Hussain Al-Qahtani, Jeddah (SA); Farid Ahmed, Jeddah (SA); Heba Al Khatabi, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/373,834

(22) Filed: Jul. 13, 2021

Related U.S. Application Data

(60) Division of application No. 17/232,544, filed on Apr. 16, 2021, which is a continuation of application No. 17/002,216, filed on Aug. 25, 2020, now Pat. No. 11,071,733.

(51) Int. Cl.
*A61K 31/47* (2006.01)
*A61P 9/10* (2006.01)
*A61K 31/4178* (2006.01)

(52) U.S. Cl.
CPC .......... *A61K 31/47* (2013.01); *A61K 31/4178* (2013.01); *A61P 9/10* (2018.01)

(58) Field of Classification Search
None
See application file for complete search history.

(56) References Cited

U.S. PATENT DOCUMENTS 11,071,733 B1 * 7/2021 Zaidi .................. A61K 31/4178

* cited by examiner

*Primary Examiner* — Jeffrey S Lundgren
*Assistant Examiner* — Michael J Schmitt
(74) *Attorney, Agent, or Firm* — W & C IP

(57) ABSTRACT

Stroke patients with comorbidities, such as diabetes, hypertension, or other conditions associated with cardiovascular, pulmonary or renal disease do not respond well to current treatments for stroke. An inhibitor of S-nitrosoglutathione reductase (GSNOR) is administered as an adjunct therapy with remote ischemic conditioning (RIC) to treat a stroke in a subject having at least one comorbidity, such as diabetes and hypertension. When performed in conjunction with GRI therapy and RIC, intravenous tissue plasminogen activator therapy (IVT) for thrombolysis and/or endovascular thrombectomy (EVT) for clot retrieval are effective in subjects with comorbidities, even after five hours post-onset of stroke.

3 Claims, No Drawings

Specification includes a Sequence Listing.

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
gatgtgctgc ctctggtctt                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ttgggatgct ccatggtcac                    20

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
acgcagagga ccttaacagt ctac               24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
gcttcacact tcacagttac ttgg               24

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gcaccttaca cctaccagag t                  21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
aaacttctgc ctgacgagct t                  21

<210> SEQ ID NO 7
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 7
tagtccttcc taccccaatt tcc                                               23

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
ttggtcctta gccactcctt c                                                 21

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
tgacagacta cctcatgaag atcc                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
acatagcaca gcttctcttt gatg                                              24
```

GSNO REDUCTASE INHIBITOR AS AN ADJUNCT THERAPY WITH REMOTE ISCHEMIC CONDITIONING AND THROMBOLYTIC REPERFUSION THERAPIES IN STROKE

BACKGROUND OF THE INVENTION

Field of the Invention

The invention generally relates to a treatment for stroke when remote ischemic conditioning is not effective. The invention further relates to a method for repurposing an inhibitor of S-nitrosoglutathione reductase as an adjunct therapy to delayed or late IVT (beyond 3 hours) in stroke, particularly for ischemic stroke with comorbidities.

Background

Acute ischemic stroke (AIS), often due to a thromboembolic (TE) occlusion in cerebral arteries, results in reduced cerebral blood flow (CBF), brain tissue hypoxia/ischemia and subsequent progression of cerebral infarction and brain cell death. To date, the FDA has approved only two reperfusion therapies in AIS: intravenous tissue plasminogen activator therapy (IVT) for thrombolysis within 3 hours of stroke and endovascular thrombectomy (EVT) for mechanical clot retrieval. These two therapies re-open large occluded blood vessels and reinstate CBF in them. However, neither IVT nor EVT guarantee the restoration of microcirculatory reflow, which is critically needed to eventually reoxygenate the ischemic region. Thus, despite a successful reperfusion therapy in stroke, brain tissue hypoxia may persist, which remains a critical barrier in improving post-stroke outcomes. Therefore, ischemic stroke remains a significant cause of adult mortality and a leading cause of adult disability worldwide. The FDA and NIH/NINDS stroke research progress related committees strongly recommend the development and repurposing of existing therapies to treat stroke (Fisher et al. Stroke 2009, 40(6):2244-2250). It is also recommended that the new promising adjunct therapy should be effective alone to reduce ischemia-reperfusion (IR) injury, should be safe to utilize as a field therapy without requiring any state-of-art facilities such as in remote community hospitals for primary care, during transport in ambulance, Emergency Department and any acute care situation. Most importantly, a new and/or repurposed therapy also should not contradict and prevent the use of IVT/EVT.

Nitric oxide (NO) is a freely diffusible endogenous small molecule which is produced by the NO-synthase (NOS) enzymes. Endothelial NOS (eNOS) remains the major producer of vascular/endothelial NO which relaxes vascular smooth muscles cells and improves tissue oxygenation. Endogenous NO can be present as nitrate ($NO_3^-$)/nitrite ($NO_2^-$) or preserved as s-nitrosylated proteins (—SH to —SNO) such as glutathione GSH>GSNO and hemoglobin Hb>HbSNO. Thus, GSNO and HbSNO were recognized as the major chariots and sources of bioactive endogenous NO in the form of —SNO adducts. Exogenous NO-inhalation, which increases levels of GSNO/HbSNO, was one of the earliest therapies incidentally identified to treat angina and later tested in ischemic stroke (Lundberg et al. Nat Rev Drug Discov. 2008; 7(2):156-167). However, NO-inhalation therapy increases risk of blood pressure lowering which can cause hemorrhagic transformation (HT) to worsen stroke outcomes. On the other hand, NO in the form of conventional $NO_3^-/NO_2^-$ therapy recently showed no benefits in stroke clinical trial (Bath et al. Cochrane Database Syst Rev. 2017; 4:CD000398).

Others and we recently reported that remote ischemic conditioning (RIC) modulates endogenous NO-metabolome, enhances CBF and improves outcomes after stroke/ischemic brain injuries (Hess et al. Acta Neurochir Suppl. 2016; 121:45-48; Hoda et al. Stroke. 2012; 43(10):2794-2799; Hoda et al. Transl Stroke Res.2014, 5(4):484-90). However, it remains a concern that in a larger population of stroke patients often accompanied with most common comorbidities (such as hypertension and diabetes), RIC may fail to protect. Indeed, it is evident from a latest preliminary small clinical trial report that RIC therapy remained neutral in effect in stroke patients, likely indicating that the "no-effects" outcome in comorbid stroke patients might have neutralized or skewed the overall outcome of the trial (Pico et al. Int J Stroke. 2016; 11(8):938-943).

Thus, there is a need for an adjuvant treatment that can enhance benefits of the current FDA-approved reperfusion therapies to further improve functional outcomes after stroke. Compounding this lack of treatment options, most exogenous therapies have failed in stroke trials in the past four decades aside from IVT/EVT, so the problem of microcirculatory no-reflow persists. In particular, there is a need for an effective treatment for patients with comorbidities to improve recovery from stroke and reduce ischemic brain injury by promoting reperfusion and restoring microcirculatory flow because comorbidities such as diabetes alters the vascular patency and increases the risk of HT during ischemic stroke, particularly in response to late IVT.

SUMMARY OF THE INVENTION

The invention is a method of treatment for a stroke and is particularly suited for treating a subject who also has at least one comorbid condition, such as diabetes and/or hypertension. The treatment comprises administering a therapeutically effective amount of an S-nitrosoglutathione reductase (GSNOR) inhibitor, wherein the therapeutically effective amount is sufficient to inhibit brain tissue injury. The GSNOR inhibitor is an adjunct therapy to be administered in conjunction with the RIC therapy, particularly in stroke with comorbidities such as stroke patients accompanied with diabetes and/or hypertension. GSNOR inhibitors that may be used include N6022, cavosonstat, N91115, N6338, as well as any other GSNOR inhibitor. The GSNOR inhibitor may be administered prior to performing RIC therapy or concurrently with the RIC therapy. The RIC therapy is performed according to an FDA-approved protocol and/or by using an FDA-approved device.

In one embodiment, the method further comprises the step of administering a therapeutically effective amount of IVT, wherein the therapeutically effective amount is sufficient to achieve thrombolysis, and/or administering EVT for clot retrieval. The combination of GRI therapy and RIC therapy with EVT and/or IVT is effective even when the "window of opportunity" of 3 hours has passed since the time of onset of stroke, which is when the risk of HT would otherwise will increase due to late IVT.

In another embodiment, the subject having comorbid conditions is suspected to be suffering from a stroke or is at the risk of suffering an imminent stroke with comorbidities and lacking FDA-approved reperfusion interventions (IVT/EVT) for at least 3 h. Stroke in subjects having comorbidities is particularly dangerous and more likely to result in exacerbated brain injury and HT than subjects not having comorbidities. In particular, the patient is suffering from at least one comorbid condition, such as diabetes, type II diabetes, hypertension, cardiac disease, coronary artery disease, arteriosclerosis, atherosclerosis, myocardial infarct, congestive heart failure, peripheral vascular disease, dementia, cerebrovascular disease, chronic pulmonary disease, congestive obstructive pulmonary disease, kidney disease, kidney failure, chronic liver disease and metabolic syndrome. In one embodiment, the subject is suffering from the comorbid conditions of diabetes and hypertension, and the GSNOR inhibitor is administered as an adjunct therapy to RIC therapy to enhance the efficacy and benefits of RIC. Optionally, IVT and/or EVT are also administered to dissolve and/or remove a thrombus or blood clot from an artery, thereby restoring perfusion of the brain region in which blood flow was being blocked by the thrombus/clot.

As a result of the treatment, ischemic injury and brain tissue infarct can be reduced, minimized or avoided, and functional activity that would otherwise be impaired is restored, at least in part. Functional activities in humans include cognitive, speech and motor skills that are needed for normal everyday living and contribute to quality of life.

In one embodiment, the invention is a method of restoring brain microcirculatory flow in a subject suffering from at least one comorbid condition, comprising the step of administering in combination of an RIC therapy and a therapeutically effective amount of an GSNOR inhibitor, wherein the therapeutically effective amount is sufficient to allow reperfusion of a brain region wherein the brain microcirculatory flow was previously blocked. The GSNOR inhibitor may be administered prior to initiation of the RIC therapy, or the GSNOR inhibitor may be administered concurrently with delivery of the RIC therapy.

In another embodiment, the invention is a method of restoring brain microcirculation in a subject suffering from at least one comorbid condition, comprising the step of administering in combination RIC therapy and a therapeutically effective amount of an GSNOR inhibitor, wherein the therapeutically effective amount is sufficient to allow reperfusion of a brain region wherein the brain microcirculatory flow was previously blocked. Optionally, the RIC and GRI therapy may be followed by administration of IVT for thrombolysis and/or EVT for clot retrieval.

Other features and advantages of the present invention will be set forth in the description of invention that follows, and in part, will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 1A-1D shows the effect of embolic middle cerebral artery (MCA) occlusion (eMCAo) on GSNOR protein expression and activity. 1A shows semi-quantitative densitometry of an immunoblot for GSNOR protein normalized to β-actin protein in whole brain tissue for sham-operated group. 1B shows a representative immunoblot for GSNOR expression in whole brain tissue. 1C shows an activity assay based on the rate of GSNO-dependent consumption of NADH in brain. 1D shows an activity assay of rate of GSNO-dependent consumption of NADH in plasma.

FIGS. 2A-2D show the effect of GRI therapy in aged male mice following photothrombotic (PT) stroke, a thrombotic model of moderate injury. 2A shows a representative image of whole brain collected immediately after stroke to confirm the site of occlusion in MCA region. 2B shows a Z-projection of T2-weighted magnetic resonance image 48 h after stroke. Site of thrombotic occlusion and stroke injury in 2A and 2B, respectively, are indicated with arrow. 2C shows densitometry of coronal sections from brains of treated mice, and 2D shows representative TTC-stained set of coronal sections (2-µm thick) obtained from the whole brain and stained freshly.

FIGS. 3A-3D show that a sex difference was found in the basal level of plasma GSNOR activity. 3A shows GSNOR activity in males and females. 3B shows plasma GSNOR activity in aged females after PT-stroke. 3C shows densitometry of infarct volume measured in coronal sections, and 3D shows a representative TTC-stained set of coronal sections (2 mm thick) obtained from the whole brain and stained freshly.

FIGS. 4A-4D show analyses of mice in a stroke model of permanent MCA occlusion (pMCAo). 4A shows a representative grey scale laser speckle contrast image (LSCI) immediately after stroke. A narrow beam walk test was used to determine any deterioration of motor function for walking time to traverse through the beam length, shown in 4B, and number of foot slips, shown in 4C. 4D shows % CBF for males and ovariectomizedfemales (OVX-Fem) treated with vehicle (Veh) or GRI therapy.

FIGS. 5A-5B show representative LSCI images from mice treated with vehicle or GRI therapy. Males are represented in 5A and OVX-female mice are represented in 5B.

FIGS. 6A-6D show representative real-time perfusion plots. 6A is vehicle-treated male; 6B is a GRI therapy treated male; 6C is a vehicle-treated OVX-female; and 6D is a GRI therapy treated OVX-female.

FIGS. 7A-7B show analyses of males and OVX-females treated with vehicle or GRI therapy. 7A shows TTC-staining of fresh brain tissue and 7B shows infarct volume analysis.

FIGS. 8A-8B show representative LSCI images and real-time perfusion curve during ischemia (8A) and reperfusion (8B), in the transient MCA occlusion (tMCAo) model of stroke and restoration of CBF.

FIGS. 9A-9D show representative real-time electrogram traces for mice treated with combinations of vehicle or GRI and RIC-mock or RIC therapy (RIC-Thr).

FIG. 10A-10B analyses of mice treated with combination vehicle or GRI and RIC-mock or RIC therapy. 10A shows a plot of the linear regression and 10B shows reoxygenation of brain tissues (PbtO2) for each treatment combination.

FIGS. 11A-11D show inflammatory gene expression in brains of mice treated with combinations of vehicle or GRI and RIC-mock or RIC therapy (N=6/gp). 11A shows measurement of iNOS expression; 11B shows measurement of iCAM; 11C shows measurement of IL-1β; and 11D shows measurement of IL-6.

FIGS. 12A-12D show that GRI therapy enhanced the neuroprotective efficacy of RIC therapy in reperfused tMCAo stroke model in streptozotocin (STZ)-induced diabetic mice. 12A shows % infarct volume following treatment, and 12B shows % swelling, and 12C shows infarct volume in GRI+RIC combination therapy group, vehicle-mock operated control, GRI therapy singly and RIC therapy alone. 12D shows representative TTC-stained fresh brain tissue images wherein GRI therapy in combination with RIC therapy enhanced neuroprotection in the tMCAo model with the comorbidity of diabetes.

FIGS. 13A-13B show analyses of mice treated with vehicle, GRI, IVT or GRI+IVT. 13A shows stroke injury/edema volume quantification. 13B shows representative coronal slices from the MCA region.

FIGS. 14A-14B show neurological deficit scoring (NDS) and survival. 14A shows NDS based on a modified Bederson Scale performed for all surviving mice at 96 h post-eMCAo in treatment groups of vehicle, GRI, IVT or GRI+IVT. 14B shows a Kalan-Meier survival curve for all 4-groups followed for 2-weeks.

FIGS. 15A-15B show tests for long-term functional outcomes for mice treated with vehicle, GRI, IVT or GRI+IVT. 15A shows recovery of muscular-strength (hanging wire test) and 15B shows protection of learning-memory function (novel object recognition test).

FIG. 16 shows representative series of fixed brain samples from mice treated with vehicle, GRI, IVT or GRI+IVT at day-15 post-eMCAo.

DETAILED DESCRIPTION

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

The invention is a method of treatment for stroke and, in particular, it is a treatment for stroke in a subject or patient who has at least one comorbid condition. This is a patient population that is particularly predisposed to stroke, with comorbid conditions that complicate medical management of conventional treatments, and will be likely treated with RIC, EVT, IVT and/or any possible combinations of these 3 therapies The method of the invention enhances and preserves endogenous —SNO, a bioactive form of NO that improves microvascular flow during hypoxia/ischemia without altering blood pressure. A key benefit of the invention is that it extends the effective safe window of thrombolysis with intravenous tissue plasminogen activator (IVT) therapy beyond the current 3 hours post-onset of stroke when the risk of hemorrhage/HT is elevated and IVT is not approved beyond this window of 3 hours, particularly in stroke patients with comorbidities.

In one embodiment, the invention is a method of treatment for a stroke in a subject in need thereof, comprising administering a therapeutically effective amount of an GSNOR inhibitor, wherein the therapeutically effective amount is sufficient to inhibit brain tissue injury, as an adjunct therapy with RIC therapy. Known GSNOR inhibitors include N6022, cavosonstat, N91115 and N6338. Any of these inhibitors are suitable for the method of the invention. The GSNOR inhibitor may be administered prior to performing RIC therapy or it may be administered concurrently with the RIC therapy. The RIC is performed according to an FDA-approved protocol and/or by using an FDA-approved device.

In another embodiment, the method further comprises the step of administering a therapeutically effective amount of IVT, wherein the therapeutically effective amount is sufficient to achieve thrombolysis, and/or administering EVT for clot retrieval. The method is surprisingly effective even when the "window of opportunity" (e.g., 3 hrs) has passed since a suspected time of onset of the stroke and the chance of hemorrhage would otherwise by increased.

In another embodiment, the subject is suspected to be suffering from a stroke or is expected to have higher brain injury and worsened outcomes (such as stroke with diabetes, hypertension etc.) and/or hemorrhagic transformation. Stroke in subjects having comorbidities is particularly dangerous and likely to result in exacerbated brain injury worsening outcomes due to the comorbid condition(s). In particular, the treatment may be administered prophylactically if a stroke or higher brain injury or hemorrhagic transformation appears imminent when a patient also suffers from at least one comorbid condition.

The method of the invention comprises a combination therapy that was surprisingly effective in patients whose symptoms are resistant to conventional treatments. This resistance arises from the complex underlying conditions of comorbidity, such as, type II diabetes, hypertension, cardiac disease, coronary artery disease, arteriosclerosis, atherosclerosis, myocardial infarct, congestive heart failure, peripheral vascular disease, dementia, cerebrovascular disease, chronic pulmonary disease, congestive obstructive pulmonary disease, kidney disease, kidney failure, chronic liver disease and metabolic syndrome. A patient with even one of these conditions is frequently refractory to all currently available treatments procedures, and presents a higher risk of complications and poor outcomes, both from the stroke itself and/or procedures to treat stroke. In one embodiment, the subject has one of these comorbid conditions, and in other embodiments, the subject has many of these comorbid conditions.

In one embodiment, the subject is suffering from the comorbid conditions of diabetes and hypertension, and the GSNOR inhibitor is administered as an adjunct therapy to RIC therapy. Optionally, IVT and/or EVT are also administered to dissolve and/or remove a thrombus or blood clot from an artery, thereby restoring perfusion of the brain region in which blood flow was being blocked by the thrombus/clot. As a result of the treatment, ischemic injury and brain tissue infarct can be reduced, minimized or avoided, and functional activity that would otherwise be impaired is preserved or restored, at least in part.

In one embodiment, the invention is a method of restoring brain microcirculatory flow in a subject suffering from at least one comorbid condition, comprising the step of administering in combination with RIC therapy and a therapeutically effective amount of an GSNOR inhibitor, wherein the therapeutically effective amount is sufficient to allow reperfusion of a brain region wherein the brain microcirculatory flow was previously blocked. The GSNOR inhibitor may be administered prior to initiation of the RIC therapy, or the GSNOR inhibitor may be administered concurrently with RIC therapy.

In another embodiment, the invention is a method of restoring brain microcirculatory flow in a subject suffering from at least one comorbid condition, comprising the step of administering in combination a therapeutically effective amount of an GSNOR inhibitor, wherein the therapeutically effective amount is sufficient to allow reperfusion of a brain region wherein the brain microcirculatory flow was previously blocked, and RIC therapy, and these are followed by administration of IVT for thrombolysis and/or EVT for clot retrieval.

As used herein, the term "GRI therapy" refers to administration or delivery of a GSNOR inhibitor.

As used herein, the term "RIC therapy" refers to administration or delivery of remote ischemic conditioning (in regimens of pre, per and/or post conditionings), a medical procedure that aims to reduce the severity of ischemic injury to an organ such as the heart or the brain, most commonly in the situation of a heart attack or a stroke, or during procedures such as heart surgery when the heart may temporary suffer ischemia during the operation, by triggering the body's natural protection against tissue injury. The procedure involves repeated, temporary cessation of blood flow to a limb to create ischemia in the tissue. This "conditioning" activates the body's natural protective physiology against reperfusion injury and the tissue damage caused by low oxygen levels. It typically can be administered or performed using a simple blood pressure cuff, or it can be performed using a device designed for this purpose, such as one currently in review at the FDA.

As used herein, the term "intravenous tissue plasminogen activator therapy" or "IVT" refers to a medical procedure involving administration of an FDA-approved intravenous thrombolytic (IVT). Tissue plasminogen activator (tPA), is an intravenous medicine given during ischemic stroke, i.e., in a stroke caused by a blood clot, wherein IVT can dissolve the stroke-causing clot. Studies have shown that certain stroke patients who receive tPA within 3 hours, have better outcomes. IVT is currently FDA-approved for use only within the initial 3 hours window of post-ictus.

As used herein, the term "endovascular thrombectomy" or "EVT" refers to a medical procedure for mechanical removal of a thrombus (blood clot) under image guidance using a catheter type device. A thrombectomy is most commonly performed for an arterial embolism, which is an arterial blockage often caused by atrial fibrillation, a heart rhythm disorder, blood clot etc.

As used herein, the term "biopharmaceutical compound" may be considered different from a "synthetic pharmaceutical compound", and may include a non-immunogenic adeno-associated virus carrying a transgene to genetically intervene and inhibit GSNO-reductase for long-term benefits via genetic intervention.

As used herein, the term "pharmaceutically acceptable" means any molecular entity or composition that does not produce an adverse, allergic, or other untoward or unwanted reaction when administered to an individual. As used herein, the term "pharmaceutically acceptable composition" is synonymous with "pharmaceutical composition". A pharmaceutical composition of the invention may be used for human and veterinary applications. In a preferred embodiment of the invention, a composition of the invention is administered to humans, most preferably to children. The pharmaceutical compositions of the invention may be administered to an individual alone, or in combination with other active ingredients.

The invention is a method of treatment to enhance and preserve endogenous —SNO, a bioactive form of NO that improves microvascular flow during hypoxia/ischemia without altering blood pressure (Stamler et al. Science 1997, 276(5321):2034-2037; Shu et al. Cell Mol Life Sci 2015, 72(23):4561-4575). Thus, the invention is a method of treatment or therapy to protect against stroke injury and improve benefits of RIC therapy in stroke with comorbidity. Of interesting note here, —SNO, the endogenously preserved vasoactive NO, s-nitrosylates tPA to enhance the effects of IVT in stroke treatment (Stamler et al. *Proc Natl Acad Sci USA*. 1992, 89(17):8087-8091). GSNOR is an endogenous enzyme and the master regulator which balances the endogenous level of —SNO by degrading/reducing GSNO (Jahnova et al. *Plants (Basel)*. 2019; 8(2)). Thus, an increased activity of GSNOR may deplete endogenous NO level during stroke and therapies such as RIC therapy. Without being bound by theory, it is believed that the method of the invention counteracts this depletion of endogenous NO that is caused by increased GSNOR activity.

Acute ischemic stroke, often due to TE occlusion, is the most common (~87%) type of strokes. Microcirculatory reflow after stroke is essential for the reoxygenation of ischemic penumbra and to prevent infarct progression. Despite reperfusing "large" vessels with the FDA-approved stroke therapies, reoxygenation of brain frequently remains incomplete, and hence, a critical barrier to improve post-stroke outcomes. Microcirculation is notably enhanced with freely diffusible vasculo-humoral NO, which improves tissue perfusion during hypoxia; however, a recent clinical trial concluded no benefits from a conventional $NO_3^-/NO_2^-$ therapy in stroke. Moreover, a risk of blood pressure BP lowering remains warranted with the long-term use of exogenous NO-therapy. Therefore, an objective of the invention is the enhancement and preservation of "endogenous" NO-metabolome for microvascular protection in stroke. Endothelial NO synthase (eNOS) activity prominently constitutes the vascular NO-pool that enhances microcirculation. Genetic impairment or deletion of eNOS in mice augmented microvascular dysfunction and brain tissue hypoxia during ageing and also exacerbated injury after acute stroke; thus, the critical role of endothelial NO was established in microvascular perfusion and resultant neuroprotection. Following injury, eNOS expression decreases in micro-vessels and activity is concomitantly impaired; however, NO generated or delivered remotely was found transportable to a distant ischemic organ resulting in improved microcirculation via hypoxic vasodilation. Thus, myocardial overexpression of eNOS protected against ischemia-reperfusion (IR) injury in liver in an experimental model. This mechanism of NO preservation and carriage also involves s-nitrosylation/trans-nitrosylation of thiol group of proteins (—SH>—SNO) such as glutathione (GSH) and hemoglobin (Hb) within red blood cells; thereby, s-nitrosylated GSH (GSNO) and Hb (HbSNO) were recognized as the major endogenous chariots of bioactive NO which protect against hypoxia and IR-injuries. Intravenous GSNO-therapy and increased HbSNO with NO-inhalation improved outcomes in stroke models. Furthermore, —SNO-therapy reduced embolization in human patients, attenuated secondary ischemia after sub-arachnoid hemorrhage, and of particular interest, induced hypoxic vasodilation to enhance cerebral blood flow in rodents; however, a risk of increased injury remains associated at certain doses of exogenous GSNO in stroke.

The enzyme GSNO reductase (GSNOR or ADH5) is a class III alcohol dehydrogenase which degrades —SNO/GSNO. Genetic deletion and pharmacological inhibition of GSNOR protected against IR-injury due to increased endogenous level of —SNO. A GSNOR inhibitor preserved vasculo-protective benefits of low-level endogenous NO in hypertension, one of the most common comorbidities associated with ageing and stroke. GRI therapy, in hypertensive rats with impaired NO production, preserved flow-mediated dilation and protected against microvascular and conduit artery dysfunction. GRI therapy also protected against mechanical reperfusion injury in brain; however, the effect of stroke on GSNOR expression/activity particularly in a clinically relevant TE-stroke model has been previously unknown, as have any potential benefits of its modulation in different stroke models, ages, sexes and reperfusion dynamics. The examples of the invention will demonstrate the effectiveness of the methods disclosed herein.

Vasculo-humoral NO is decreased during acute stroke in both, rodents and human patients. Others and we have reported that therapies capable of modulating endogenous NO-metabolome, such as RIC, enhances cerebral blood flow, protects against ischemic brain injuries, and improved efficacies of late IVT in stroke. Of note, NO following s-nitrosylation of tissue plasminogen activator (tPA) promotes thrombolysis. Herein, the examples of the invention will further demonstrate that TE-stroke upregulates GSNOR expression/activity, which in turn, will attenuate endogenous —SNO level and augment stroke injury. Furthermore, examples of the invention demonstrate that GRI therapy in stroke will preserve endogenous —SNO to augment microcirculation, improve benefits of reperfusion to reoxygenate brain and attenuate injury to improve functional outcomes.

GSNOR inhibitors are known and have been used in investigational studies of ischemia and reperfusion. For example, Khan et al. (*Brain Res*. 2020 Aug. 15; 1741: 146879.) teaches that mice were treated with N6022 (5 mg/kg) at 2 hr post ischemia/reperfusion, daily for 3 days or 2 weeks. Neurological score, survival rate and motor/cognitive skills were improved. However, these results were not performed in clinically relevant thromboembolic stroke model nor were they validated in different stroke models. While Khan mimics conditions of a specific minor population of stroke patients reperfused following mechanical EVT, EVT alone does not guarantee microvascular perfusion and brain tissue reoxygenation. Furthermore, Khan fails to teach or suggest IVT, RIC, or any combination of any adjuvants with RIC/IVT. Landman et al. (Stroke Vol 50; 7, 2019 p 19534-1939) teaches the hypothesis that RIC induces the release of humoral factors including NO, which activate afferent neural and humoral pathways and shows that RIC reduces oxidative damage and suppresses inflammatory responses in the brain. However, Landman fails to make any connection of RIC to other therapies or consider subjects having comorbidities.

The GSNOR inhibitor may be administered via any suitable route, including but not limited to intravenous, intranasal, nebulization, oral, intramuscular, caudal, intrathecal, and subcutaneous. Compositions comprising GSNOR inhibitors include any pharmaceutically-acceptable carrier or buffer suitable for administration to a subject. In a preferred embodiment, the pH of the composition is in the range of 6.5 to 8.2 or 6.5 to 8.0 or 6.5 to 7.0. In another preferred embodiment, the pH of the composition is in the range of 6.6 to 8.2 or 6.6 to 8.0 or 6.6 to 7.0. In a preferred embodiment, the pH is 6.6, 6.7, 6.8 or 6.9. In a more preferred embodiment, the pH is 6.7 or 6.8. In a further preferred embodiment, the pH is 6.8. In another more preferred embodiment, the pH is 7. In a particularly preferred embodiment, the pH is 6.8 and the buffer strength is 0.05 M. In another particularly preferred embodiment, the pH is 7.0 and the buffer strength is 0.02 M. Various buffers may be used to prepare a pharmaceutical composition of the invention, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. In a preferred embodiment, the buffer is sodium citrate buffer. In a more preferred embodiment, the sodium citrate buffer comprises tri-sodium citrate, citric acid and purified water. In another preferred embodiment, the buffer is phosphate buffer. Preferably, the buffer strength is in the range of 0.01 to 0.1 M or 0.01 to 1 M. More preferably the buffer strength is 0.01 M to 0.06 M. In a further preferred embodiment, the buffer strength is 0.02 M to 0.06 M, more preferably 0.02 M to 0.05 M and most preferably 0.02 M or 0.05 M. The active ingredients and/or excipients can be soluble or can be delivered as a suspension in the desired carrier or diluent. In a preferred embodiment of the invention, the liquid pharmaceutical composition is a solution.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary designs and methods for fabricating and using microgrippers of the invention. These Examples describe materials and methods for using embodiments illustrated in FIGS. 1-16. Additional details can be found in the section entitled "Brief Description of the Drawings".

The following Examples of the invention are provided to demonstrate that TE-stroke enhances GSNOR expression/activity, which in turn, will attenuate endogenous —SNO level and augment stroke injury. The Examples also demonstrate that GRI therapy for stroke will preserve endogenous —SNO to augment microcirculation, improve benefits of reperfusion to reoxygenate brain and attenuate injury to improve functional outcomes.

Models of Stroke

The following models of stroke were used in the Examples of the invention to demonstrate methods of treatment.

The eMCAo Model of TE-Stroke

Human fibrinogen-supplemented clot was prepared to induce TE-stroke as reported by Hoda et. al. Briefly, under isoflurane anesthesia, the right common carotid artery (CCA), external carotid artery (ECA) and internal carotid artery (ICA) were exposed with blunt dissection. A modified microcatheter containing a $9.0 \pm 0.5$-mm long clot was inserted into the right ECA, advanced into the ICA and the clot was gently delivered into the MCA region along with 100 µL of 1× sterile phosphate buffered saline (PBS). The catheter was retracted, the ECA-arteriotomy was ligated to prevent bleeding, and wounds were sutured. Sham-operated mice underwent a similar procedure including infusion of 100 µL of 1× sterile PBS without a clot. Mice were returned to clean warm recovery cages until conscious and were given free access to NAPA-gel and chow diets along with water ad-libitum until sacrifice.

The Photothrombotic (PT)-Model of Stroke

Aged mice ($16 \pm 1$-mo) were subjected to PT-stroke via a novel lateral side surgical approach without craniotomy resulting in the thrombotic occlusion of distal main trunk of MCA. For the purpose, mice were anesthetized with isofluorane, prepared for surgery, and rose Bengal dye (50 mg/kgbwt in 200 uL of 1× sterile PBS) was intravenously (IV) infused. Mice were immediately put on a robotic stereotaxic frame, the head was rotated to face right side up, and the skull was exposed. The distal trunk of MCA was visualized underneath the skull bone (without craniotomy) using a 532 nm laser source (8-mm beam diameter; 4.5 mW) integrated to an ID8-iris (ThorLabs, NJ, USA). The MCA region above the zygomatic arc was exposed with the laser for 20-min from a distance of ~2-3-mm. Following 20-min laser exposure, thrombotic occlusion of the distal trunk of MCA was confirmed using laser doppler flowmeter showing>60% drop in CBF and finally the lateral side skin wound was closed.

The pMCAL Model of Stroke

The procedure for pMCAo was performed in mice as reported by Hoda et al. (Stroke 2012, 43(10):2794-2799). Briefly, under anesthesia, the junction of left zygomatic arch and squamous bone was drilled to make a 2-3 mm burr hole to expose the main trunk of MCA. The left MCA distal to the lenticulostriate branches was electrocauterized carefully without bleeding. The wound was closed, and mice were put under post-op recovery as described above. Sham-operated group underwent similar surgical procedures but without electrocauterization.

The Reperfused tMCAo Model of Stroke

The tMCAo surgical procedure is similar to TE-stroke surgery, however, the transient occlusion is achieved using a suture instead of a clot as reported by Hoda et al (supra). Briefly, a 6-0 monofilament suture with ~3-mm silicone-coated tip designed to induce tMCAo in mice (Doccol Corp, USA) was introduced into the ICA via an ECA stump, directed and gently advanced into the MCA region until the suture was wedged to occlude the proximal stem of MCA. The occlusion was maintained prior to withdrawing the filament after 45 minutes, the ECA-arteriotomy was ligated and the reperfusion was allowed following suture withdrawal. The sham-operated group underwent similar procedures without occlusion, and mice recovered as above.

Materials and Methods

Animal Models and Experimental Approach

All mice under C57/B6 background were bred, housed, used and related experimental procedures were performed in accordance with the approved protocol of Institutional Animal Care and Use Committees (IACUCs) of St. Joseph's Hospital and Medical Center (SJHMC), and Augusta University, Augusta, Ga. Effect of stroke on GSNOR expression/activity was first determined in a clinically relevant partially-humanized TE-stroke, embolic middle cerebral artery occlusion (eMCAo) model in aged ($16 \pm 1$-mo-old) male mice. Next, an effective dose-finding study of GRI therapy (stroke injury size) was performed in aged ($16 \pm 1$-mo-old) male mice in a photothrombotic (PT) model of stroke with the reduction in infarct volume as the primary outcome. The safety and benefits of the best dose of GRI therapy in reducing infarct volume as the primary outcome was also confirmed in reproductively senescent aged ($16 \pm 1$-mo-old) female mice subjected to PT-stroke. To test the benefits of GRI therapy during permanent ischemia, GRI was also tested in adult ($14 \pm 1$-weeks) mice of both sexes subjected to permanent model of middle cerebral artery ligation (pMCAL). All females were ovariectomized at the age of 12-weeks, i.e., 2-weeks prior to stroke surgery. A 2×2 factorial design was adopted [2 Sexes (MALE vs. FEMALE)×2 GRI (NO vs. YES)] such that all 4 groups of both sexes were subjected to pMCAL followed by randomization into two different treatment cohorts: GRI therapy or equal volume of Vehicle treatment. All mice were tested for behavioral outcome on a narrow beam test, relative CBF measurement using laser speckle contrast imaging (LSCI) and infarct volume size. Next, benefit of GRI therapy was tested with and without RIC therapy in preserving benefits of endogenous NO in a reperfused stroke model in diabetic male mice ($14 \pm 1$-weeks). RIC therapy has been reported to enhance CBF in stroke models likely via enhancing endogenous NO but remains untested in comorbid (such as diabetic) stroke, a patient population which are least benefited from the FDA-approved reperfusion therapies such as endovascular thrombectomy (ET). To mimic a clinical ET-like scenario, GRI therapy was tested in a reperfused transient MCA occlusion (tMCAo) model of stroke. A 2×2 factorial design was adopted [2 GRI (NO vs. YES)×2 RIC (NO vs. YES)] such that all 4 groups were subjected to tMCAo followed by randomization into 4 different treatment cohorts: Vehicle, GRI, RIC and GRI+RIC. Outcome measures such as brain tissue oxygenation (PbtO2), acute inflammatory genes response, neurological deficit, edema as percent (%) swelling and infarct volumes were assessed. Lastly, GRI therapy was also tested with and without late-IVT, an FDA-approved thrombolytic reperfusion therapy, in eMCAo for which again a 2×2 factorial design was adopted [2 GRI (NO vs. YES)×2 IVT (NO vs. YES)] as above: Vehicle, GRI, IVT and GRI+IVT groups. Adult male mice ($16 \pm 2$-weeks) were used in this experiment.

Treatments after Stroke

Briefly, different doses of GRI therapy (N6022; Axon Medchem, USA) at various time points, as indicated for each of the following Examples, were tested in different sets of experiments and stroke models. In general, GRI therapy was IV-infused via the tail vein following stroke, and IP-repeated after stroke as indicated. RIC and IVT therapies were performed as indicated. All control groups were either infused with equal volume of vehicle (for GRI- and IVT-therapies) or underwent RIC-mock for sham-operation of RIC therapy.

Laser Doppler Flowmetry (LDF) and Laser Speckle Contrast Analysis (LASCA) Imaging Cortical LDF (Perimed Inc, Sweden) was performed to confirm the induction of stroke in anesthetized mice. Briefly, mice were anesthetized as above and a shallow indent was made in the parietal skull using a low-speed drill to place the LDF probe holder (PH07-6, Perimed Inc) aligning the holder hole at the stereotaxic coordinates (AP: 2-mm and lateral 3-mm with respect to bregma). The needle of LDF-probe (PH407, Perimed Inc) was inserted into the probe holder and the signal was recorded to confirm a significant drop in CBF following stroke. Mice were anesthetized as above, body temperature was maintained at 37±0.5° C., the skull was shaved, and a midline skin incision was made to primarily expose the MCA region. Perfusion images were acquired using PeriCam high resolution LASCA-Imager (PSI-Z system, Perimed Inc.) with a 70-mW built-in laser diode for illumination and 1388×1038 pixels CCD camera installed 10 cm above the skull (speed 19 Hz, and exposure time 6 mSec, 1.3×1.3 cm). Acquired video and images were analyzed for the dynamic changes in CBF. Overall perfusion of the ipsilateral ischemic hemisphere was determined, normalized with the equal size of region of interest (ROI) from the uninjured contralateral hemisphere and the relative CBF was calculated.

MRI Acquisition

All MRI experiments were conducted using a 7-Tesla horizontal magnet with a clear bore of 20-cm in diameter interfaced to a Bruker Avance console. Anesthetized mice underwent the following MRI-fast spin echo (RARE factor=8) with effective echo time of 47 ms to create corresponding T2-weighted images to determine absolute edema/stroke injury volume. Ex vivo diffusion tensor imagining (DTI) was performed with overnight MRI of fixed brains through a pulse-gradient spin echo sequence to determine the diffusion parameters including apparent diffusion coefficient (ADC), tensor trace and fractional anisotropy (FA).

MRI Data Analysis

Image post-processing for edema was performed using ImageJ coupled with in-house designed ImageJ macro scripts. T2-weighted images were used to determine the volume of cerebral edema by drawing an irregular ROI to encircle the regions exhibiting edema in each impacted image slice. The impact volume was determined by summation of the ROIs in all the impacted image slices and then multiplying with the thickness of the image slice. DTI analysis was done using the vendor-supplied software Paravision 5.1 (Bruker Inc.), from which the associated diffusion weighted, FA and ADC images were generated.

Analysis of GSNOR Expression and Activity after Stroke

Plasma was isolated from freshly drawn blood after cardiac puncture under deep isoflurane anesthesia, and mice were sacrificed to collect brain tissue. Plasma and brain tissue samples were snap-frozen until assay.

Immunoblot Assay for GSNOR Expression

Gel electrophoresis followed by immunoblot for the GSNOR expression in brain tissue samples (perfused with 50-mL of chilled 1× sterile PBS) was performed using conventional methods. Briefly, brain homogenates in modified RIPA buffer (Upstate, Lake Placid, N.Y.), supplemented with 40-mM NaF, 2-mM $Na_3VO_4$, 0.5-mM phenylmethylsulfonyl fluoride and 1:100 (v/v) of proteinase inhibitor cocktail (Sigma), were electrophoresed and immunoblotted separately against antibodies for anti-GSNOR (Sigma), and anti-beta actin (β-Actin; Santa Cruz Biotech, USA) as loading control. Immuno-densitometric signal for GSNOR was quantified in arbitrary units (AU) using ImageJ NIH free software and was normalized with the corresponding expression of β-Actin.

GSNOR Activity Assay

A method of GSNO dependent NADH consumption was used to determine GSNOR activity as reported. Briefly, brain tissue was homogenized in a buffer containing 50 mM Tris-HCl (pH 8.0), 150 mM NaCl, 1-mM EDTA, 0.1% Triton X-100 and 1:100 protease inhibitor cocktail and centrifuged (10, 000 g×10 minutes at 4° C.) to obtain supernatant. Next, plasma and brain tissue supernatant were diluted to a protein concentration of 1 mg/mL and 0.1 mg/mL, respectively, in a reaction buffer containing 20 mM Tris-HCl (pH 8.0), 0.5 mM EDTA and 0.7504 NADH following which samples were incubated in triplicate with or without 100 μM GSNO in 96-well plate. The consumption of NADH was monitored with fluorescence spectrophotometry at an excitation wavelength of 340 nm and emission at 460 nm. GSNOR activity was calculated by subtracting the rate of NADH consumption incubated in the presence of GSNO minus the rate of NADH consumption without GSNO in samples.

Euthanasia and 2,3,5-Triphenyltetrazolium Chloride (TTC) Staining

TTC-stain differentiates between metabolically active (live or penumbra) and inactive (dead or core) tissues after stroke. TTC is a white powder and the solution remains colorless, which is reduced to red 1,3,5-triphenylformazan (TPF) by the enzymatic action of various dehydrogenases primarily mitochondrial dehydrogenase from the living tissues, while the core remains as white. Therefore, larger white area indicates higher injury and infarction volume. After performing ATT, mice were overdosed and deeply anesthetized with high isofluorane (5%). Brains were very quickly perfused with cold 25 ml of 0.01 M phosphate-buffered saline (PBS), harvested fresh and immediately placed in a metallic mouse brain matrix. Looking at the infarcted area, 5 blades were placed in alternate gaps to cut and obtain 2-μm×4 coronal slices. Sections were individually placed in a 35-mm dish containing pre-warmed (37° C.) 3-ml of 5% TTC in PBS (Sigma) for 20-25 minutes at 37° C., followed by 2× washing with cold PBS and fixation with 10% formalin. In order to image, fixed sections were taken out of the dish and placed in order on a high-resolution Cannon Scanner. After scanning, images were cropped and saved for analysis. Corrected infarct volume was estimated using gray scale image and Scion Image software and presented as the Corrected % infarct volume normalized to the uninjured side.

Behavioral Tests

Beam Walk Test for Motor Balance and Coordination

Motor balance and coordination test was performed using the narrow balance beam walk. The beam apparatus consisted of a graduated beam, was fixed 20-cm above the tabletop on two poles (6-mm flat width×125-cm long). A black box was fixed at the end of narrow beam as the finish point containing nesting (bedding) material from the home cage to attract the mouse. A lamp (with 60-watt light bulb) is used to shine light above the start point, serving as an aversive stimulus. Mice were trained to walk on the barrow beam prior to injury and before performing the post-stroke test. During training, mice were encouraged to keep moving across the beam by gently poking or pushing on their back. Training trials were repeated for 3 trials×3 consecutive days or until each animal crosses the beam 3× without stopping or turning around, and without any assistance. On a final day of testing, each mouse was tested to walk 100-cm on the beam with 3-trials×5 min interval between trials. Performance of each mouse on the narrow beam was quantified by measuring the time it took for the mouse to traverse the 100-cm distance on the narrow beam and the number of foot slips that occurred in each trial. The mean value of 3 trials was calculated for the time taken in traversing the 100-cm distance on the beam, and the number of foot faults.

Neurologic Deficit Score (NDS)

Neurologic deficits after stroke in mice were assessed by blinded investigators blinded on a 5-point modified Bederson NDS-scale. The highest number indicates the worst outcomes while lower number indicates better neurological outcomes: 0, no deficit (normal mice); 1, forelimb flexion deficit on contralateral side; 2, flexion deficit along with decreased resistance to lateral push and torso-turning to the ipsilateral side when held by tail; 3, all deficits as in Score 2 including very significant circling to the affected side during the move inside the cage and reduced capability to bear weight on the affected side; 4, all deficits as above but rarely willing to move spontaneously and preferring to stay at rest.

Hanging Wire Test for Forelimb Coordination and Muscular Strength

This test was used as a measure of grasping ability, forelimb strength and muscular coordination movements. The apparatus is consisted of a 55-cm long 1-mm diameter single metal cord stretched firmly between two metal stands, 50-cm above a standard mouse cage filled with soft paper bedding material. In the training process, mice are gently held and taken closer to the wire to grab it with their two forelimbs. Mice were trained for 3 trials×3 consecutive days before the actual test, or until they are trained to grab it with two forelimbs. For the actual test, the latency to lose the grip on the wire falling into the cage was recorded for 3 trials× 5-min interval between trials for each mouse.

Novel Object Recognition (NOR) Test for Cognitive Function

Object recognition memory is one of the domains of cognition that is often impaired in aged (non-demented) individuals as well as in patients with other forms of dementia. Importantly, the rodent NOR-task has been described as a model of (non-spatial) recognition memory. This form of memory is believed to consist of a recollected (episodic) and a familiarity component, i.e., behaviors that are demonstrated in the NOR-task when subjects explore a novel object more than a familiar one. The NOR-task has become a popular method for rodent studies with particular relevance to dementia and neuropsychiatric disorders.

Behavioral assessment by NOR test that reliably evaluates the nonspatial working memory of the subcortical region was performed 4-wks after stroke. Briefly, mice were habituated in an activity box and familiarized with two identical objects placed at a set distance apart. On the day of trial, each mouse was individually given similar trial and the time spent ($T_f$) with the familiar object was recorded. After the familiar object trial, the mouse was then removed from the environment for a set amount of time and one of the two previously used (familiar) objects was replaced with a novel object that was different from the familiar object in shape, texture, and appearance. The time spent ($T_n$) by the mouse with the novel object upon exposure during the probe trial was then recorded in one 5-min trial. This test is based on the natural tendency of mouse to investigate a novel object rather than a familiar one, which reflects the use of learning and recognition memory processes. The capability of the mouse to discriminate between a familiar vs. novel object was determined as the discrimination index, which is calculated by $DI=(T_n-T_f)/(T_n+T_f)$. A lower DI-value reflects poor cognitive function, while a higher DI-values demonstrates a better learning and memory function.

Data Analysis

Data and Statistical Analysis

Quantitative data were presented as mean±standard deviation (SD). Wherever needed, unpaired t-test was performed to determine statistical significance. A log transformation was used prior to statistical analysis as needed to stabilize variance across groups. Non-normal data between groups were compared using nonparametric asymptotic two-sided Wilcoxon rank sum test. In experiments with 2× factorial design, a factorial analysis of variance (ANOVA) with interaction between two therapies followed by post-hoc comparisons using independent t-tests was used to analyze the outcome measures. Bonferroni multiple corrections were applied in the post-hoc analysis. In the absence of a significant interaction, the main effects were considered to be additive when combined. A p-value<0.05 was considered statistically significant. All statistical analyses were conducted using STATA 15.

Data

FIG. 3E, FIG. 4B, FIG. 4D, FIGS. 6A-D, FIG. 8B, FIGS. 9A-D, and others in this description are real time curves/plots from the instrument. They are presented to show the real time output as an example from one animal. For each animal subject, the values are averaged and calculated as either a percentage (%)(e.g., for CBF/perfusion) or in mmHg for oxygen (after converting the millivolt output) and then they are plotted as the data for each group.

Example 1

Effect of eMCAo on GSNOR Protein Expression and Activity.

The eMCAo model was chosen because it is the most clinically relevant rodent model of TE stroke. Aged (16±1-mo) mice were subjected to eMCAo/stroke using a partially-humanized TE-clot. At 6 h post-eMCAo, blood was collected via cardiac puncture to isolate plasma and mice were quickly flushed-perfused with 25-mL of chilled 0.1M PBS prior to collecting brain samples. Both plasma and brain samples were snap-frozen in liquid nitrogen until assays. FIGS. 1A and 1B show whole brain assay and the resultant relative normalized densitometry data confirmed that the protein expression of GSNOR was significantly (p<0.01) increased as early as 6 h post-stroke as compared to sham-operated group. An activity assay based on the rate of GSNO-dependent consumption of NADH further confirmed that the increase in protein expression of GSNOR translated into significant (p<0.001) acute increase in the enzymatic activity of GSNOR as early as 6 h after stroke. FIG. 1C shows GSNOR activity in brain and FIG. 1D shows GSNOR activity in plasma.

Example 2

Effect of GRI Therapy in Aged Mice of Both Sexes Following PT Stroke.

The PT stroke model was chosen because it is a thrombotic model of moderate injury. FIG. 2A shows a representative image of whole brain collected immediately after stroke to confirm the site (black arrow) of occlusion in MCA region. FIG. 2B shows a Z-projection of a T2-weighted MR-image 48 h after stroke. The site of stroke injury is indicated with a white arrow. Different doses of GRI therapy or equal volume of vehicle to aged male mice (N=8/gp) given intravenously 1 h after PT-stroke (1, 2.5, 5.0 and 10 mg/kg) showed a dose-dependent neuroprotective effect. However, a plateau in the neuroprotective effect was seen beginning from the GRI dose≥2.5 mg/kg. Densitometry showing absolute infarct volume in FIG. 2C was performed on tissues sections, including those shown in FIG. 2D. FIG. 2D shows representative TTC-stained set of coronal sections (2-μm thick) obtained from the whole brain from the aged male mice and stained freshly. GRI therapy significantly protected against the stroke and prevented the infarct/injury progression as compared to vehicle treated group ($P<0.0001$). Data are presented as Mean±SD. Statistical significance was determined at $P<0.05$ and were indicated with asterisks or different letters indicating statistically different Means.

A sex difference was found in the basal level of plasma GSNOR activity, showing higher GSNOR activity in female mice compared to age-matched males ($P<0.05$; N=6/gp) as shown in FIG. 3A. Therefore, GRI therapy was also tested in aged female mice (N=10/gp). (F-H) The effective dose of GRI therapy (2.5 mg/kg) for aged male mice was tested in aged female mice as described above for males. As evident in FIG. 3B, there was a significant increase ($P<0.0001$) in plasma GSNOR activity in aged females, too, after PT-stroke. GRI therapy after PT-stroke in females significantly inhibited the post-stroke plasma GSNOR activity ($P<0.01$). GRI therapy was also effective in reducing the stroke injury significantly compared to vehicle treated group ($P<0.05$). FIG. 3D shows representative TTC-stained set of coronal sections (2-μm thick) obtained from the whole brain of aged female mice and stained freshly. Data are presented as Mean±SD. Statistical significance was determined at $P<0.05$ and were indicated with asterisks or different letters indicating statistically different Means.

Example 3

GRI Therapy Protects Against Permanent Ischemia Induced by pMCAo Independent of Sex Adult mice of both sexes (14±1-weeks; N=10/gp; females were ovariectomized, OVX) were subjected to pMCAL-stroke model with electrocauterization leading to permanent occlusion of distal MCA trunk. Mice were anesthetized with isofluorane, prepared for surgery, and the right parietal bone of the skull was exposed. A craniotomy was performed to expose the distal part of MCA trunk and the artery was permanently electrocauterized using a bipolar electrocautery. FIG. 4A shows a representative LSCI image. Immediately after stroke, a significant drop in CBF occurred. Mice were IV-treated with either GRI therapy (2.5 mg/kg) or equal volume of vehicle at 1 h after stroke and the treatment was repeated daily for 2 days.

Mice were evaluated for behavioral outcomes at 72 h post-stroke. A 2 sexes (Male vs. Female) by 2 treatments (GRI vs. Veh) ANOVA was used to analyze results. All the data are expressed as mean±SD, pairs of means indicated with different letters are significantly different ($P<0.05$). Narrow beam walk test determined that there was no significant difference in the deterioration of motor function between two sexes in the context of walking time to traverse through the beam length and number of foot slips. FIG. 4B shows the time to traverse the beam, and FIG. 4C shows the mean number of foot slips. GRI therapy was equally effective in improving motor function in both sexes.

Mice were also evaluated for CBF changes and infarct volume analysis at 72 h post-stroke. A 2 sexes (Male vs. Female) by 2 treatments (GRI vs. Veh) ANOVA was used to analyze results. Changes in CBF showed a trend toward slight differences in vehicle-treated OVX-females as evident from the plot shown in FIG. 4D.

At 72 h post-pMCAo, % CBF loss in the injured side of brain in both sexes was evident, as shown in FIG. 5A for males, and FIG. 5B for OVX-females, but was also significantly higher in OVX-females compared to males. GRI therapy improved restoration of CBF in both sexes significantly compared to their corresponding vehicle treated groups. The GRI therapy treated groups in both sexes showed no significant difference in % CBF when compared together, demonstrating that the effect of GRI therapy in enhancing CBF remains sex independent.

Real-time perfusion was measured in mice at 72 h post-stroke. FIG. 6A shows vehicle-treated males and Figure B shows GRI-treated males. FIG. 6C shows vehicle-treated OVX-females (OVX-F) and FIG. 6D shows GRI-treated OVX-females. As with the % CBF and LSCI, vehicle-treated OVX-females showed a slight trend towards difference in real-time perfusion plots. At 72 h post-pMCAo, GRI therapy treated groups in both sexes showed no significant difference in real-time perfusion plots when compared together, demonstrating that the effect of GRI therapy in enhancing CBF remains sex independent.

TTC-staining of fresh brain tissue, shown in FIG. 7A, and infarct volume analysis, shown in FIG. 7B, further demonstrates that vehicle treated OVX-females were significantly more prone to stroke injury compared to their vehicle treated male counterparts. GRI therapy significantly prevented the infarct progression sex-independently in both groups.

Example 4

GRI Therapy Improves Acute Brain Tissue Oxygenation Following Reperfusion and Enhances Benefits of RIC Therapy in STZ-Induced Diabetic Mice.

This example is a demonstration of reperfusion and restoration of oxygenation (PbtO2) in reperfused tMCAo stroke model. Diabetes was induced in adult male mice (14±1 weeks of age) as confirmed after 7 days of STZ-injection, followed by tMCAo stroke surgery at 3 weeks post-STZ injection. Stroke was induced with 60-min suture occlusion followed by reperfusion with suture withdrawal. GRI therapy or vehicle was IV-infused 10-min prior to reperfusion and RIC therapy/RIC-mock was performed 1 h after reperfusion. A 2 GRI (GRI vs. Veh) by 2 RIC (RIC therapy vs. RIC-mock) ANOVA was used to analyze results. All the data are expressed as Mean±SD, and pairs of Means indicated with different letters are significantly different ($P<0.05$).

Representative LSCI, shown in FIG. 8A, and real-time perfusion curve during ischemia and reperfusion, shown in FIG. 8B, demonstrated successful induction of stroke and restoration of CBF. These results were comparable to those shown in Example 3 using the tMCAo model. PbtO2 was measured at 6 h post-reperfusion (N=6/gp) using a 50-um thick oxygen sensor integrated to an UniAmp multi-channel system (Unisense, Denmark). Measurement signal was averaged for 3 min during a period of stable output as shown in the representative real-time electrogram traces in FIGS. 9A-9D. FIG. 9A is representative of a mouse treated with vehicle and receiving mock RIC. FIG. 9B is representative of a mouse receiving vehicle and RIC therapy. FIG. 9C is representative of a mouse receiving GRI therapy and mock RIC. FIG. 9D is representative of a mouse receiving GRI therapy and RIC therapy. PbtO2 values were calculated from the calibration curve and associated regression equation, shown in FIG. 10A. As evident from the data plot in FIG. 10B, GRI therapy alone improved PbtO2 significantly as compared to vehicle-treated RIC-mock operated group. RIC therapy alone did not improve PbtO2 in diabetic stroke as compared to vehicle-treated stroke group; however, in combination therapy group, a prior treatment with GRI followed by RIC therapy showed enhanced efficacy of both, GRI and RIC-therapies, in improving benefits of reperfusion to increase PbtO2.

Mice were immediately sacrificed after PbtO2 measurement and brain tissue samples were analyzed for inflammatory gene expression (N=6/gp). RT-PCR primers shown in Table 1 were used to measure changes in expression of iNOS (FIG. 11A), iCAM-1 (FIG. 11B), IL-1β (FIG. 11C) and IL-6 (FIG. 11D). The result for each inflammatory gene was normalized to expression of β-actin and expressed as a fold change.

Looking at the results for mice receiving a vehicle treatment instead of GRI and/or RIC, treatments including any sham component (vehicle-mock operated control, GRI-treatment singly and RIC therapy alone) did not improve any of the neurological outcomes of mean NDS, % infarct volume, or % swelling, shown in FIGS. 12A, 12B, and 12C, respectively. However, when low-dose GRI was combined with RIC therapy, all outcome measures were significantly improved in combination therapy group as compared to all other 3 groups. Representative TTC-stained fresh brain tissue images, shown in FIG. 12D, further supports the finding that GRI in combination with the NO-enhancing RIC therapy increases neuroprotection in diabetic stroke.

Example 6

GRI Therapy Protects Against TE Stroke Injury and Enhances Benefits of Late-IVT Therapy.

In this example, the TE-clot eMCAo model is used to demonstrate a method of the invention. Adult male WT-mice (16±2-weeks old; N=20/gp) were subjected to eMCAo using a partially humanized TE-clot (9±1-mm). Mice were randomized to 4-groups: 2 GRI (GRI vs. Veh) by 2 IVT (IVT vs. Veh). GRI therapy (2.5 mg/kgbwt) or equal volume of vehicle was IV-infused at 1 h post-eMCAo. The same dose of GRI therapy or equal volume of vehicle was also repeated and IP-injected after IVT or IVT-veh at 6 h and 24 h post-eMCAo. Late IVT-therapy (tPA as Altepase formulation; 10 mg/kg in 250 uL) or equal volume of vehicle was

TABLE 1

Nucleotide Sequences of Mouse Primers used for RT-PCR.

| Gene | Genbank Accession No. | Primer sequence | SEQ ID NO |
| --- | --- | --- | --- |
| iNOS | NM_010927.3 | GAT GTG CTG CCT CTG GTC TT | SEQ ID NO: 1 |
|  |  | TT GGG ATG CTC CAT GGT CAC | SEQ ID NO: 2 |
| iCAM-1 | NM_010493 | ACG CAG AGG ACC TTA ACA GTC TAC | SEQ ID NO: 3 |
|  |  | GCT TCA CAC TTC ACA GTT ACT TGG | SEQ ID NO: 4 |
| IL-1β | NM_010554.4 | GCA CCT TAC ACC TAC CAG AGT | SEQ ID NO: 5 |
|  |  | AAA CTT CTG CCT GAC GAG CTT | SEQ ID NO: 6 |
| IL-6 | NM_031168.1 | TAG TCC TTC CTA CCC CAA TTT CC | SEQ ID NO: 7 |
|  |  | TTG GTC CTT AGC CAC TCC TTC | SEQ ID NO: 8 |
| β-actin | NM_007393 | TGA CAG ACT ACC TCA TGA AGA TCC | SEQ ID NO: 9 |
|  |  | ACA TAG CAC AGC TTC TCT TTG ATG | SEQ ID NO: 10 |

GRI therapy alone showed a trend only to downregulate most inflammatory genes and were not significantly different from the vehicle-treated stroke group. Surprisingly, RIC therapy alone enhanced inflammatory responses in stroke-induced diabetic mice; however, in the combination GRI+RIC therapy group, prior treatment with GRI significantly downregulated and prevented RIC-induced inflammatory responses in diabetic stroke mice as compared to the RIC therapy alone group.

Example 5

GRI Enhances Neuroprotective Efficacy of RIC Therapy in tMCAo-STZ-Induced Diabetic Mice.

Diabetic adult male mice (as described in Example 4) were subjected to tMCAo (N=10/gp) with or without GRI and/or RIC-therapies and outcome measures were performed at 24 h post-stroke. A 2×2 factorial ANOVA was used to analyze results, data are expressed as Mean±SD, indicating Means with different letters are significantly different (P<0.05).

infused at 5 h post-eMCAo as 10% of volume IV bolus and remaining over a period of 20 min. A 2 GRI (GRI vs. Veh) by 2 IVT (IVT vs. Veh) ANOVA was used to analyze results, as appropriate. All the data are expressed as mean±SD, and pairs of means indicated with different letters are significantly different (P<0.05).

For stroke injury/edema volume measurement, 6 surviving mice from each group were randomly selected for T2-Weighted MRI at 24 h post-eMCAo. As evident from the volume quantification shown in FIG. 13A, early GRI therapy alone after stroke prevented the edema progression significantly as compared to Veh-treated group and also in comparison to late-IVT therapy. The representative coronal slices from the MCA region shown in FIG. 13B further support the quantitative finding shown in FIG. 13A. Moreover, as anticipated, late-IVT therapy did not prevent the edema progression/stroke injury significantly as compared to Veh-treated group. However, treatment with GRI therapy after eMCAo and prior to tPA-injection enhanced the benefits of late IVT and prevented edema progression significantly as compared to both, Veh- and IVT-treated groups.

Neurological deficit scoring (NDS) based on a modified Bederson Scale was performed for all surviving mice at 96 h post-eMCAo. As evident from the mean NDS values shown in FIG. 14A, early GRI therapy alone after stroke reduced the later neurological deficit significantly as compared to both Veh- and late-IVT-treated groups. Late-IVT therapy failed to improve the neurological score; however, GRI therapy in combination with late-IVT therapy significantly improved the neurological outcomes at 96 h post-stroke. Kalan-Meier survival curve for all 4 groups followed for 2 weeks. As evident from the curve shown in FIG. 14B, both groups without a GRI treatment showed higher mortality within the initial 5 days (acute/sub-acute phase) after stroke with a prominent trend in mortality in late-IVT treated group. A higher trend in mortality in late-IVT treated group is likely attributed to frequent hemorrhagic transformation, as indicated (asterisk) in the representative coronal section for IVT-group in FIG. 14B.

On day 13 & 14, all surviving mice were tested for long-term functional outcomes such as the recovery of muscular strength (hanging wire test), shown in FIG. 15A, and protection of learning/memory function (NOR test), shown in FIG. 15B. In agreement with the benefits of acute protection, GRI therapy alone and in combination with late-IVT therapy significantly improved and protected the long-term motor and learning/memory functions, respectively, compared to both Veh- and late-IVT-treated groups. As such, late-IVT beyond 4.5 h post-stroke remained ineffective in improving long-term functional outcomes as compared to Veh-treated mice.

At day-15 post-eMCAo, all mice were sacrificed after behavioral outcome tests and brains were harvested. Q-ball MRI (DTI, T1-Intensity and DWI sequences) of randomly assigned representatives of each group was performed ex vivo using fixed brain samples. Results are shown in representative series of sections for each treatment group in FIG. 16. As evident from the appearance of the injured hemisphere (stroked ipsilateral side), both Veh- and late-IVT-treated groups demonstrated higher cerebral atrophy, larger ventricle size and greater loss in white matter (WM; corpus callosum) integrity. In contrast, GRI-treated groups with and without late-IVT showed preservation of WM-integrity, reduced cerebral atrophy and decrease in ventricle size enlargement.

The foregoing examples of the invention demonstrate the following novel findings:

1. The changes in expression and activity GSNOR have never been investigated and reported in stroke models, particularly in the most clinically relevant partially humanized TE stroke model. For the first time, these examples demonstrate that GSNOR expression/activity is increased within 3-6 hours after stroke.
2. A dose-escalation study for GRI therapy with validation in different stroke models, different ages and sexes, and various dynamics of reperfusion, has never been performed. For the first time, the Examples of the invention demonstrate differential effects of GRI therapy in various clinically relevant settings, such as different dynamics of reperfusion (permanent occlusion, partial reperfusion, complete reperfusion simulating IVT and EVT), aged vs young rodents, and male vs female.
3. The GRI therapy has not previously been tested in any kind of comorbid (diabetic, hypertensive) stroke models with or without reperfusion. For the first time, the Examples of the invention demonstrate therapeutic benefits of GRI therapy in comorbid strokes models in both, reperfused and non-reperfused stroke models.
4. RIC therapy is a modulator of endogenous NO level and a recent outcome report informs that the overall benefit of RIC therapy was neutral, i.e., without any benefits. Of note, a large population of stroke patients have comorbidities (Pico et al. *Int J Stroke*. 2016; 11(8):938-943 (see also, pubmed.ncbi.nlm.nih.gov/31500849, pubmed.ncbi.nlm.nih.gov/31621833, pubmed.ncbi.nlm.nih.gov/27412192, and pubmed.ncbi.nlm.nih.gov/29748420)). The Examples of the invention provide the first demonstration that RIC therapy alone is not protective in comorbid stroke models. These Examples also demonstrate for the first time that in comorbid (diabetic/hypertensive) strokes, performing GRI therapy prior to RIC enhances the benefits of RIC, turning it into an effective therapy in ischemic stroke with comorbidity.
5. Since it is important to demonstrate the safety of GRI therapy with the FDA-approved IVT, The Examples also demonstrate for the first time that the GRI therapy in combination with IVT therapy in the most clinically relevant partially humanized TE stroke model enhances the benefits of IVT and extends its safe window of thrombolysis.
6. Using state-of-art live animal imaging (MRI and LASCA) and in vivo brain tissue oxygenation recording techniques, the Examples of the invention demonstrate for the first time that GRI therapy improves microcirculation and brain tissue oxygenation.

In summary, the methods of the invention demonstrate the efficacy of GRI therapy as an adjunct therapy administered with RIC therapy in different models of stroke, particularly comorbid stroke, and under various clinically relevant conditions. GRI therapy showed a dose dependent differential effect, enhanced neurovascular protection and behavioral outcomes, and remain safe and beneficial with FDA-approved therapies and therapies under trial such as RIC.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGMENT

"This project was funded by the National Plan for Science, Technology and Innovation (MAARIFAH)—King Abdulaziz City for Science and Technology—the Kingdom of Saudi Arabia—award number (14-MED2597). The authors also, acknowledge with thanks Science and Technology Unit, King Abdulaziz University for technical support".

We claim:

1. A method of treating a hypertensive subject who is suffering a blockage of brain microcirculatory flow caused or suspected to be caused by a thromboembolic stroke, comprising the steps of
performing a remote ischemic conditioning (RIC) therapy to induce production of endogenous nitric oxide, and
while performing the RIC therapy, administering a therapeutically effective amount of an S-nitrosoglutathione reductase (GSNOR) inhibitor (GRI therapy) selected from the group consisting of N6022, cavosonstat, N91115 and N6338, wherein the therapeutically effective amount of GSNOR inhibitor is sufficient to preserve and enhance the activity of the endogenous nitric oxide and inhibit brain tissue injury; and
administering thereafter and intravenous tissue plasminogen activator therapy (IVT) for thrombolysis, wherein the therapeutically effective amount of the IVT is sufficient to dissolve a thrombus or a blood clot from an artery,
wherein the RIC therapy, the GRI therapy and the IVT reduce the risk of reperfusion injury in the hypertensive subject.

2. The method of claim 1, wherein the GSNOR inhibitor is N6022.

3. The method of claim 1, wherein the hypertensive subject also suffers from diabetes or type II diabetes.

* * * * *